US008409076B2

(12) United States Patent
Pang et al.

(10) Patent No.: US 8,409,076 B2
(45) Date of Patent: Apr. 2, 2013

(54) DEVICE FOR LAPAROSCOPIC OR THORACOSCOPIC SURGERY

(75) Inventors: Ah San Pang, Singapore (SG); Chong Jin Ong, Singapore (SG); Chee Kong Chui, Singapore (SG)

(73) Assignees: Mport Pte Ltd, Singapore (SG); National University of Singapore, Singapore (SG)

( * ) Notice: Subject to any disclaimer, the term of this patent is extended or adjusted under 35 U.S.C. 154(b) by 1244 days.

(21) Appl. No.: 12/095,059

(22) PCT Filed: Oct. 19, 2006

(86) PCT No.: PCT/SG2006/000308
§ 371 (c)(1),
(2), (4) Date: Sep. 5, 2008

(87) PCT Pub. No.: WO2007/061386
PCT Pub. Date: May 31, 2007

(65) Prior Publication Data
US 2009/0005636 A1    Jan. 1, 2009

(30) Foreign Application Priority Data

Nov. 28, 2005   (SG) ................ 200507710-2

(51) Int. Cl.
*A61B 1/04* (2006.01)
*A61B 1/00* (2006.01)
(52) U.S. Cl. ............... 600/109; 600/112; 600/102
(58) Field of Classification Search .......... None
See application file for complete search history.

(56) References Cited

U.S. PATENT DOCUMENTS

| 5,595,562 | A  |   | 1/1997  | Grier |
|-----------|----|---|---------|-------|
| 5,604,531 | A  |   | 2/1997  | Iddan et al. |
| 5,609,565 | A  | * | 3/1997  | Nakamura ............. 600/229 |
| 5,653,677 | A  | * | 8/1997  | Okada et al. .......... 600/112 |
| 6,428,469 | B1 |   | 8/2002  | Iddan et al. |
| 7,066,879 | B2 |   | 6/2006  | Fowler et al. |
| 2001/0035902 | A1 |   | 11/2001 | Iddan et al. |
| 2002/0103417 | A1 | * | 8/2002  | Gazdzinski ............ 600/109 |
| 2003/0114731 | A1 | * | 6/2003  | Cadeddu et al. ........ 600/114 |
| 2003/0167000 | A1 | * | 9/2003  | Mullick et al. ........ 600/424 |
| 2004/0068204 | A1 | * | 4/2004  | Imran et al. ........... 600/593 |
| 2005/0014994 | A1 |   | 1/2005  | Fowler et al. |
| 2005/0165449 | A1 |   | 7/2005  | Cadeddu et al. |
| 2005/0228283 | A1 | * | 10/2005 | Gifford et al. ......... 600/459 |
| 2006/0149135 | A1 | * | 7/2006  | Paz ...................... 600/201 |
| 2007/0129624 | A1 | * | 6/2007  | Gilad et al. ........... 600/407 |
| 2007/0161855 | A1 | * | 7/2007  | Mikkaichi et al. ...... 600/113 |
| 2007/0255100 | A1 | * | 11/2007 | Barlow et al. ......... 600/114 |

(Continued)

FOREIGN PATENT DOCUMENTS
JP        8-256973        10/1996

*Primary Examiner* — John P Leubecker
*Assistant Examiner* — Arnaldo Torres Diaz
(74) *Attorney, Agent, or Firm* — Merchant & Gould P.C.

(57) ABSTRACT

A device (10) for laparoscopic or thoracoscopic surgery, the device (10) comprising: a first member (20) to be moved across the body (5) of a patient; and a second member (30) to be placed within the body (5), the second member (30) comprising an image capturing device (32) to capture images from within the body (5) and to transmit the captured images for display; wherein the second member (30) is in magnetic engagement with the first member (20) such that the movement of the second member (30) within the body (5) is in response to movement of the first member (20) across the body (5).

28 Claims, 7 Drawing Sheets

U.S. PATENT DOCUMENTS

| | | | |
|---|---|---|---|
| 2008/0004634 A1* | 1/2008 | Farritor et al. | 606/130 |
| 2008/0058835 A1* | 3/2008 | Farritor et al. | 606/130 |
| 2009/0054909 A1* | 2/2009 | Farritor et al. | 606/130 |
| 2010/0113872 A1* | 5/2010 | Asada et al. | 600/102 |
| 2011/0034795 A9* | 2/2011 | Gilad et al. | 600/407 |
| 2011/0245596 A1* | 10/2011 | Paz | 600/37 |

* cited by examiner

DEVICE FOR LAPAROSCOPIC OR THORACOSCOPIC SURGERY

TECHNICAL FIELD

The invention concerns a device for laparoscopic or thoracoscopic surgery.

BACKGROUND OF THE INVENTION

Diagnostic laparoscopy is a procedure that allows a health care provider to look directly at the contents of a patient's abdomen or pelvis, including the fallopian tubes, ovaries, uterus, small bowel, large bowel, appendix, liver, and gallbladder.

The purpose of this laparoscopy is to actually see if a problem exists that has not been found with noninvasive tests. Inflammation of the gallbladder (cholecystitis), appendix (appendicitis), pelvic organs (pelvic inflammatory disease), or tumors of the ovaries may be diagnosed laparoscopically.

A laparoscope is an instrument through which structures within the abdomen and pelvis are visible by the surgeon during laparoscopy. A small surgical incision or port is made in the abdominal wall, for example, below the navel, to permit the laparoscope to enter the abdomen or pelvis. The laparoscope typically has a diameter of 5 to 10 mm and is in the form of a long and narrow rod. It uses a high intensity light, such as xenon or halogen, and 3-chip technology to observe the inside of the abdomen on a high resolution video screen. The laparoscope is manipulated after entry via the port within the abdomen to direct the view seen by the surgeon.

Due to the physical structure and profile of the laparoscope, it often obstructs free movement of the surgeon during surgery. During lengthy surgical procedures, this may cause the surgeon discomfort by having to manoeuvre himself or herself around the laparoscope. It is also difficult for the surgeon to perform the surgery in an ergonomic friendly manner since one of the surgeon's arms must arch across the laparoscope to manipulate a contralateral operating instrument.

One port is solely used by the laparoscope. Other ports are for surgical instruments, usually for the left and right hand of the surgeon. Thus at present, at least three ports are required for surgery. In some cases, four to six ports may be required. It is therefore desirable to minimise the number of ports required to make surgery less invasive and reduce patient trauma.

Similar problems are encountered in thoracoscopic surgery with a thoracoscope.

U.S. Pat. No. 7,066,879 discloses a relatively large bulky device insertable into a structure having a lumen that includes a first housing, at least one functional element for use during a minimal access procedure, and a securing element for removably securing the insertable device to or against a wall of structure having a lumen. U.S. Pat. No. 7,066,879 discloses that the securing element may be used to secure the insertable device to the abdominal wall with corresponding magnets placed outside the body to hold the device against the abdominal wall, a clamp, an adhesive substance. U.S. Pat. No. 7,066, 879 is primarily concerned with securing the inserted device to a fixed position on the abdominal wall. U.S. Pat. No. 7,066,879 suffers from one disadvantage in that it does not permit easy movement of the inserted device within the body once it has been fixed to the abdominal wall by the clamp or adhesive substance.

SUMMARY OF THE INVENTION

In a first preferred aspect, there is provided a device for laparoscopic or thoracoscopic surgery, the device comprising:

a first member to be moved across the body of a patient; and a second member to be placed within the body, the second member comprising an image capturing device to capture images from within the body and to transmit the captured images for display;

wherein the second member is in magnetic engagement with the first member such that the movement of the second member within the body is in response to movement of the first member across the body.

The captured images may be transmitted wirelessly to a display device.

Power may be supplied to the second member for the image capturing device by any one from the group consisting of: wirelessly from a power source, and a battery provided to the second member.

The second member may be operatively connected to a display device and a power source via at least one flexible cable, and the cable provides convenient retrieval of the second member from within the body of the patient.

The first member may comprise an electromagnet or permanent magnet or a combination of an electromagnet and permanent magnet. The strength of the magnetic force may be varied to facilitate the movement of the second member.

The image capturing device may be a digital video camera.

The second member may comprise a light emitting means to illuminate within the body.

The second member may comprise an electromechanical probe to extract bodily tissue or to deliver drugs.

The electromechanical probe may be a biopsy needle for tissue extraction.

A viewing angle of the image capturing device may be adjustable by a first control provided on the first member.

The first control may control an actuator with an embedded controller in the second member.

The orientation of the second member may be varied by changing the orientation of the first member.

The orientation of the second member may be varied using two magnets of different polarities for magnetic engagement of both first and second members.

The orientation of the second member may be varied by depressing the second member against the body to alter the viewing angle.

Image settings of the image capturing device may be adjustable by a second control provided on the first member, the image settings being any from the group consisting of: zoom, focus, contrast, and brightness.

The light intensity of the light emitting means may be adjustable by a third control provided on the first member.

The device may further comprise a magnetic shield to limit undesirable magnetic interference to the image capturing device.

The device may be introduced into the body via a primary trocar using a handling device.

The handling device and an attachment unit of the second member may enable releasable engagement of the second member through any port.

The device may be fixed relative to the body using a flexible mechanical arm.

The mechanical arm may be fastened to a side of the patient/surgical bed.

In a second aspect, there is provided a system for laparoscopic or thoracoscopic surgery, the system comprising:

at least one device comprising: a first member to be moved across the body of a patient; and a second member to be placed within the body, the second member comprising an image capturing device to capture images from within the body and to transmit the captured images for display, the second member further comprising an assembly for operative attachment to a handling device;

wherein the second member is in magnetic engagement with the first member such that movement of the second member within the body is in response to movement of the first member.

The handling device may be a rigid forceps or a customized device with a pair of pincers or tongs, for seizing and holding objects, or a modified rigid laparoscopic device with a camera located at a removed proximal end of the laparoscopic device.

The handling device may comprise a mechanism for deploying, re-positioning and retrieving the second member into and from the body through an opening provided by a trocar.

The handling device may manipulate the second member when the handling device and second member are operatively attached together.

In a third aspect, there is provided a system for laparoscopic or thoracoscopic surgery, the system comprising:

at least two devices, each device comprising: a first member to be moved across the body of a patient; and a second member to be placed within the body, the second member comprising an image capturing device to capture images from within the body and to transmit the captured images for display; the second member is in magnetic engagement with the first member such that the movement of the second member within the body is in response to movement of the first member across the body;

wherein the at least two devices provide at least two different views within the body.

The at least two different views may be displayed at the same time on a display device.

One of the at least two different views may be selectable using a touch screen selection panel that has labeled the at least two different views on the touch screen.

BRIEF DESCRIPTION OF THE DRAWINGS

An example of the invention will now be described with reference to the accompanying drawings, in which.

DETAILED DESCRIPTION OF THE DRAWINGS

Figure 1:
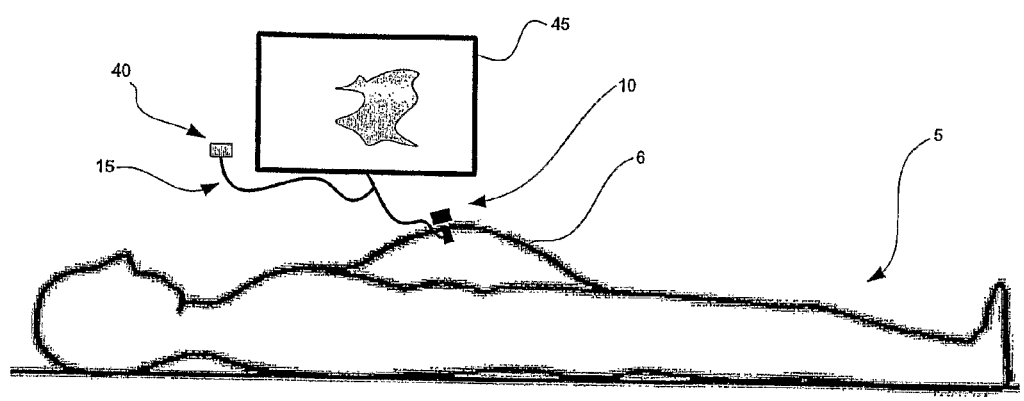
FIG. 1 is an illustration of a patient where a device, in accordance with a preferred embodiment of the present invention, has been inserted within the body.

Referring to the drawings, a device 10 for laparoscopic surgery or thoracoscopic surgery is provided. The device 10 comprises: a first member 20 and a second member 30. The first member 20 is moved across the body 5 of a patient. The second member 30 is placed within the body 5, beneath the abdominal wall 6. The second member 30 comprises an image capturing device 32 to capture images from within the body 5 and to transmit the captured images for display to a display device 45 such as a monitor. The second member 30 is in magnetic engagement with the first member 20 such that the movement of the second member 30 within the body 5 is in response to movement of the first member 20 across the body 5.

The first member 20 comprises an electromagnet 21. Supply of electrical current to the electromagnet 21 is adjustable to selectively control the strength of the electromagnetic field. Power via an electrical cable 22 from a DC power supply 40 is required to supply electrical current to the electromagnet 21. Alternatively, the first member 20 may comprise a permanent magnet. The first member 20 may be a combination of electrical and permanent magnets.

Figure 3:
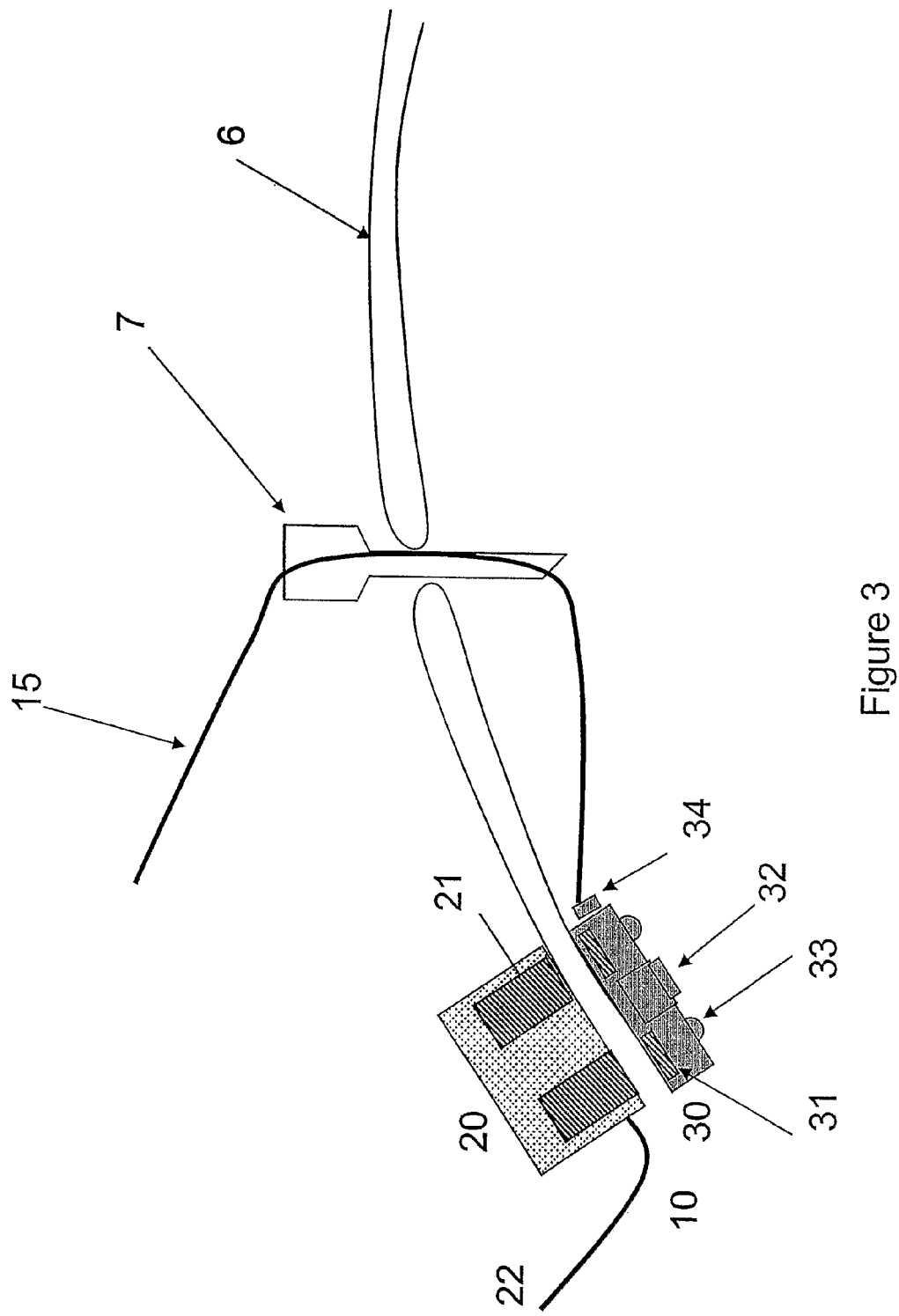
FIG. 3 is an exploded view of FIG. 1 typically with punctured method of primary trocar introduction.
Figure 4:
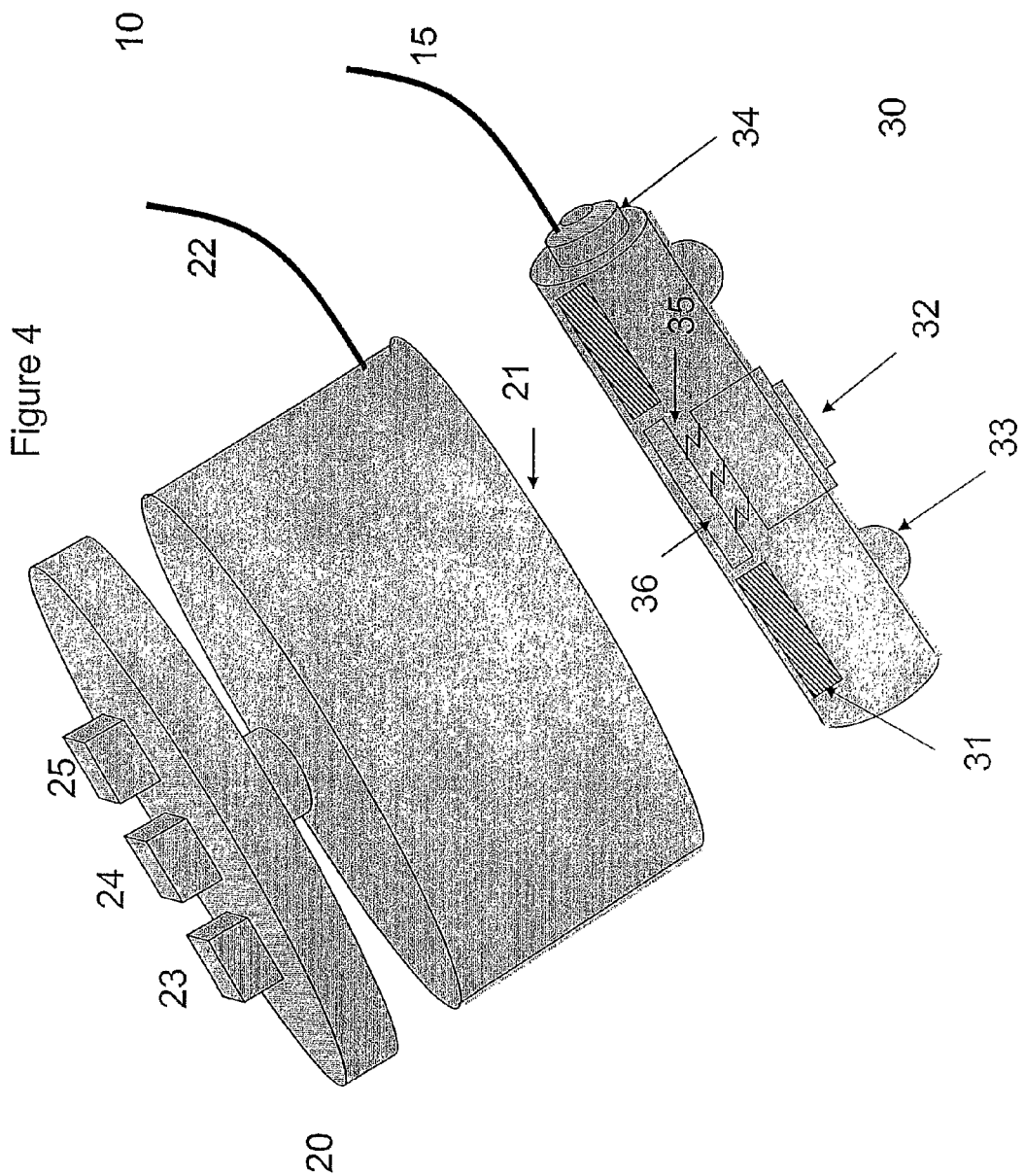
FIG. 4 is a perspective view of the device of FIG. 1.
Figure 5:
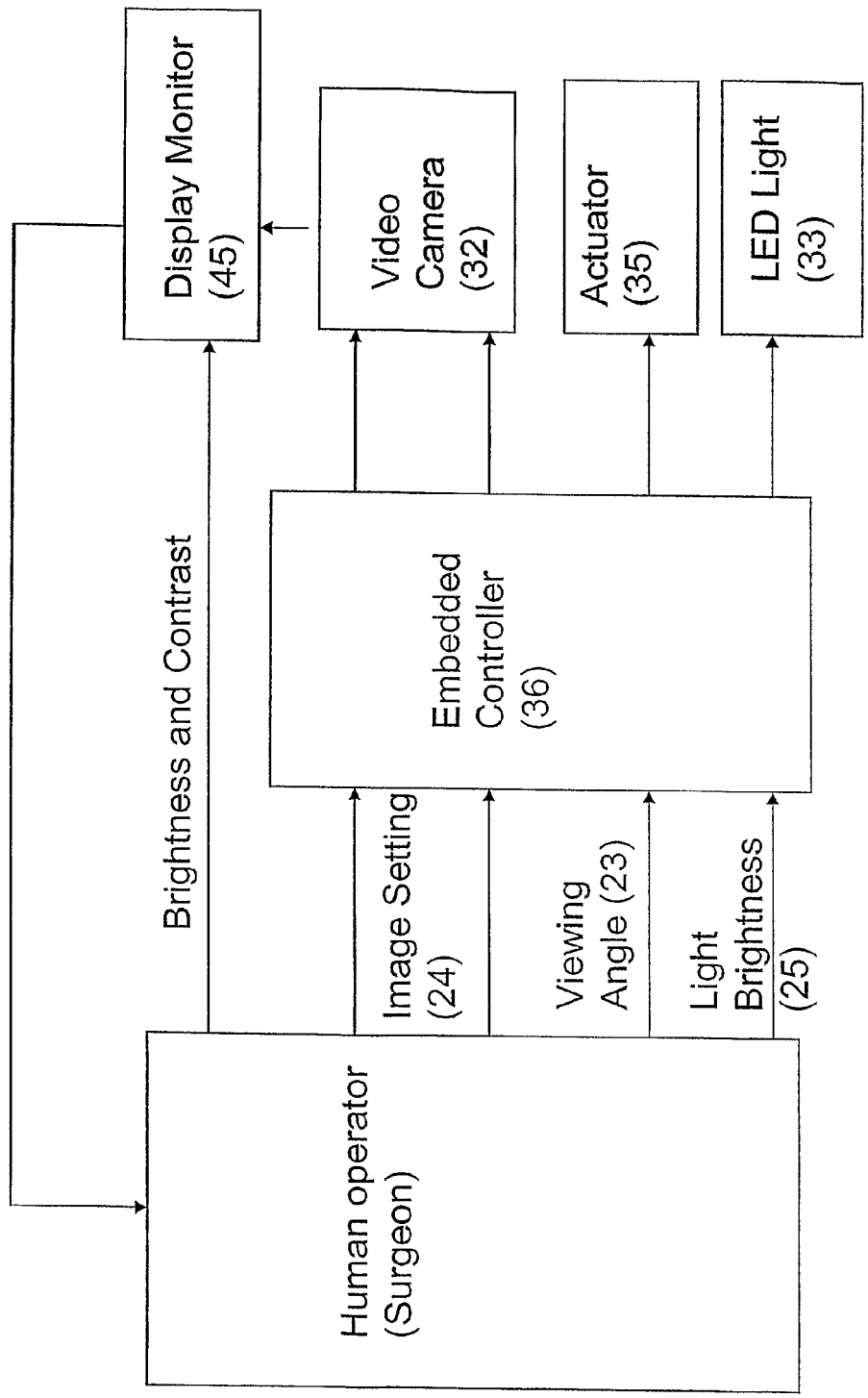
FIG. 5 is an illustration of the control mechanism for the device of FIG. 1.

The second member 30 comprises a portion 31 at its base that is made from a magnetic material. The base portion 31 is made from a ferromagnetic material such as iron (Fe), nickel (Ni), cobalt (Co) or gadolinium (Gd), or alloys of such materials. The base portion 31 is in magnetic engagement with the first member 20, and thus the position and orientation of the image capturing device 32 faces away from the wall 6. As shown in FIG. 3, the base portion 31 is made of two magnets of different polarity, in a similar arrangement as the electromagnet 21 in the first member 20. This allows the orientation of the second member 30 to change by rotating the first member 20. Apart from the base portion 31, other parts of the second member 30 may be made of a non-magnetic material so that magnetic engagement is ensured only between the first member 20 and base portion 31. By depressing the second member 30 against the body, the view direction of the first member 20 may be altered.

The first and second members 20, 30 may each have a communications module to enable communication between one another. If communication is performed wirelessly, the communications module may encode the radio signal to identify a pair of first and second members 20, 30 for a device 10. Otherwise communication is performed over a wire or cable.

The image capturing device 32 is a digital video camera. The camera 32 is able to capture colour images with at least a frame rate of thirty frames per second for real-time display. The viewing angle of the camera 32 can be changed via pitch and yaw movement achieved through an actuator 35, and is adjustable by a first control 23 provided on the first member 20. This allows the surgeon to view different areas within the body 5 without having to move the first member 20. Image settings of the camera 32 are adjustable by a second control 24 provided on the first member 20. The image settings include: zoom, focus, contrast and brightness. This allows the surgeon to obtain an improved view as desired.

The actuator 35 in the second member 30 may be a piezoelectric motor. The piezoelectric elements of the motor apply a directional force to an axle, causing it to rotate.

The second member 30 comprises a light emitting means 33 to illuminate within the body. The light emitting means may be a circular arrangement of LEDs 33 located around the periphery of the camera lens 32. The LEDs 33 illuminate the area of interest within the body 5. The light intensity of the LEDs 33 is adjustable by a third control 25 provided on the first member 20.

Preferably, the controls 23, 24, 25 communicate wirelessly with the second member 30 to control the actuator 36, camera 32 and LEDs 33, respectively. Bluetooth, WiFi or other wireless protocols are used to transmit instructions from the controls 23, 24, 25 to the second member 30. An embedded processor 36 is provided for the implementation of the control processes.

In one embodiment, the captured images are transmitted wirelessly to the display device 45. Again, Bluetooth, WiFi or other wireless protocols may be used to feed the image data to the display device 45. Power is supplied to the second member 30 for the camera 32 wirelessly from a power source or a battery provided to the second member 30. For example, RF power may be beamed from the first member 20 to the second member 30 by means of a directive antenna. It is a relatively lossless process. The power is also used for the LEDs 33 and for transmitting the captured images. The camera 32 requires power to operate and to transmit the captured images for display to the surgeon.

In another embodiment, the second member 30 is operatively connected to the display device 45 and power source 40 via at least one flexible cable 15. The cable 15 provides convenient retrieval of the second member 30 from within the body 5 of the patient.

A magnetic shield is used to limit undesirable magnetic interference to the camera 32 and image data transmitter of the second member 30. The magnetic shield may be made from a material consisting of an 80% nickel alloy, and surround a portion of the camera 32 and image data transmitter.

In one embodiment, the strength of the electromagnetic field is changed temporarily when movement of the first member 20 is desired to enable the second member 30 to move more securely. As some frictional forces will be encountered by the second member 30 when it is moved against the inner side of the wall 6, increasing the electromagnetic field slightly may make engagement more secure. If a permanent magnet is used, the magnetic force is varied by adjusting the distance between the magnets 21, 31.

In a typical scenario, the second member 30 is inserted within the body 5 at the start of the surgical procedure. In order to perform a laparoscopic or thoracoscopic procedure, at least two access ports are created in the abdominal wall 6 to gain access within the patient's body 5. The second member 30 is inserted via a first access port.

There are two ways to create a first access port, the "blind" puncture and the Hasson open method. In the "blind" puncture, carbon dioxide gas is introduced into the abdominal cavity (creating a pneumoperitoneum) through a Veress needle, a process called insufflation. Insufflation elevates and holds the abdominal wall 6 away from the internal structures and organs. A sharp trocar/cannula combination is then inserted through the abdominal or chest wall 6. The trocar is removed while the cannula 7 is left in place. In one example, through this cannula 7, the second member 30 is inserted within the body 5 using the handling device 50. Other, secondary access ports are then created, in a similar fashion with a trocar/cannula combination but under direct vision using the second member 30. Operating instruments are then inserted through the cannulae, and the operation is performed.

Figure 6:
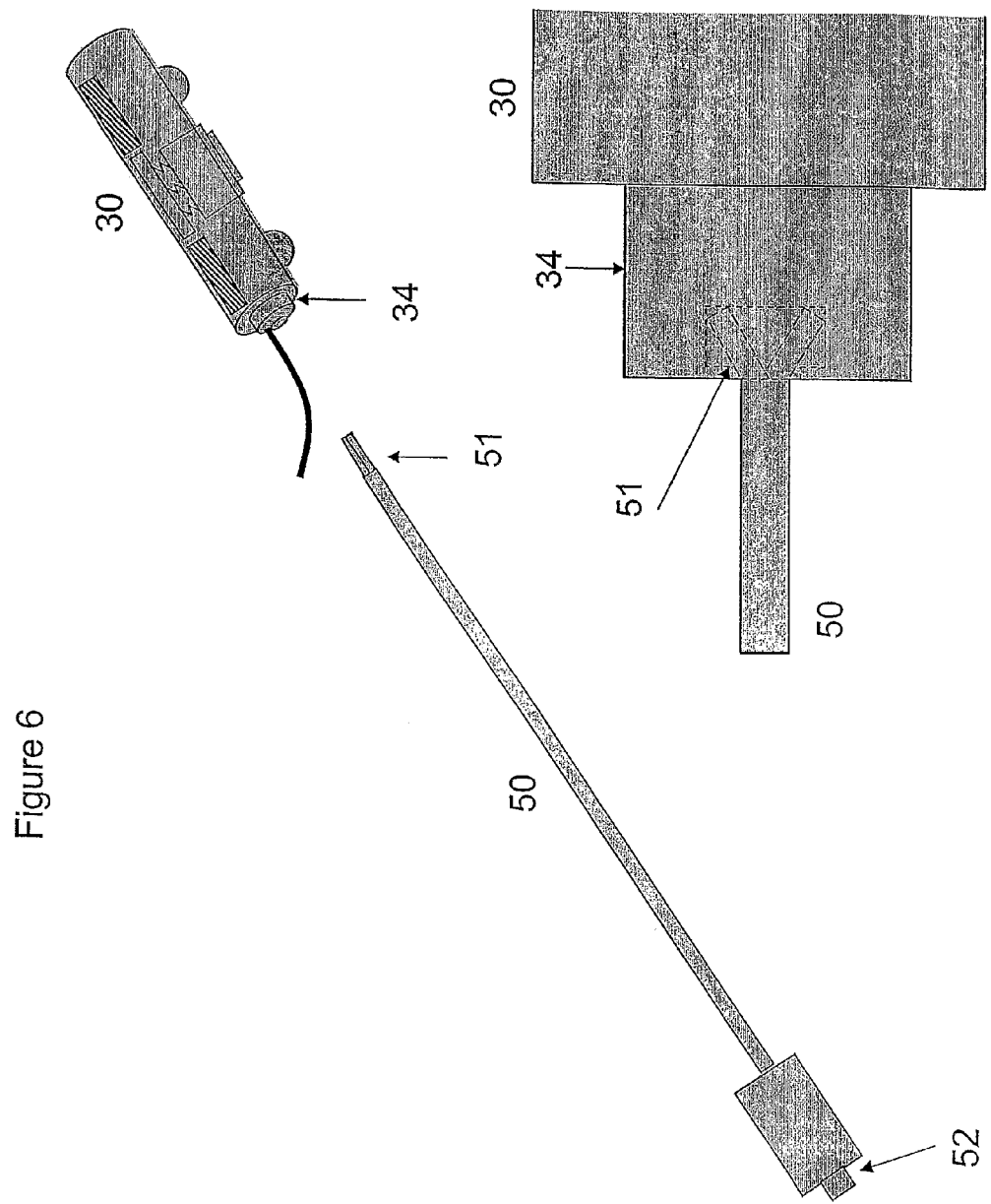
FIG. 6 is a perspective view of the handling device for the second member of device of FIG. 1.
Figure 7:
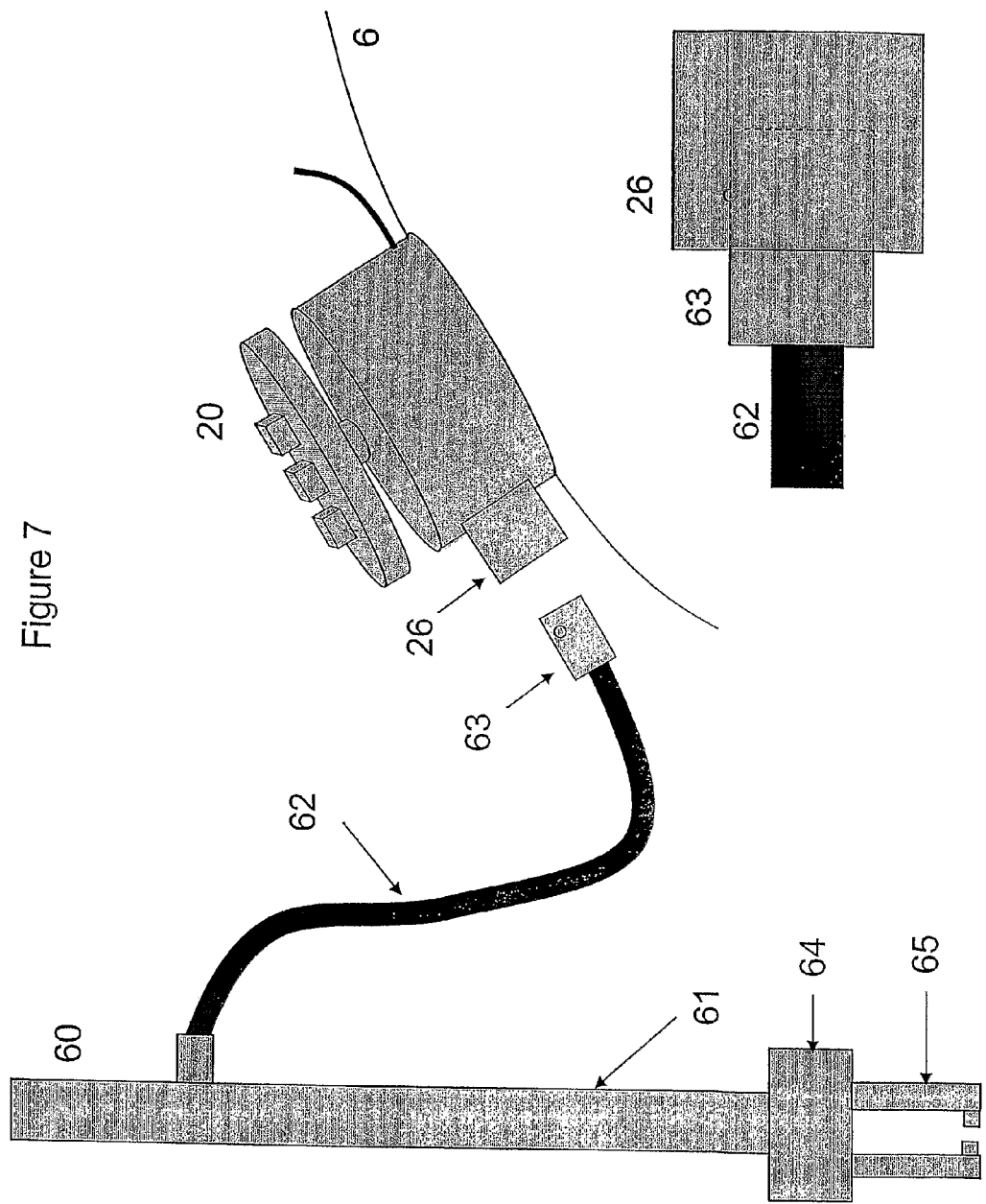
FIG. 7 is a perspective view of the holding device for the first member of device of FIG. 1.

Referring to FIG. 6, the handling device 50 is a conventional laparoscopic forceps or comprises a forceps 51 and a button 52 with a long stainless steel stem. There is an attachment unit 34 in the second member 30. The attachment unit 34 has a small opening for a proper engagement with forceps 51. The button 52 controls the opening and closing of the forceps 51, allowing engagement and disengagement of the forceps 51 to the second member 30. The handling device 50 may be docked with the second member 30 via the secondary access ports. When the handling device 50 is operatively attached to the second member 30, this enables visualization of an internal organ in all quadrants like a conventional laparoscopic camera. The handling device 50 also enables the second member 30 to be re-positioned within the body 5. The wire 15 runs through the trocar as shown in FIG. 3. The arrangement of the handling device 50 and the second member 30 may be considered a detachable laparoscopic device. A single handling device 50 may operate with a plurality of second members 30.

Figure 2A:
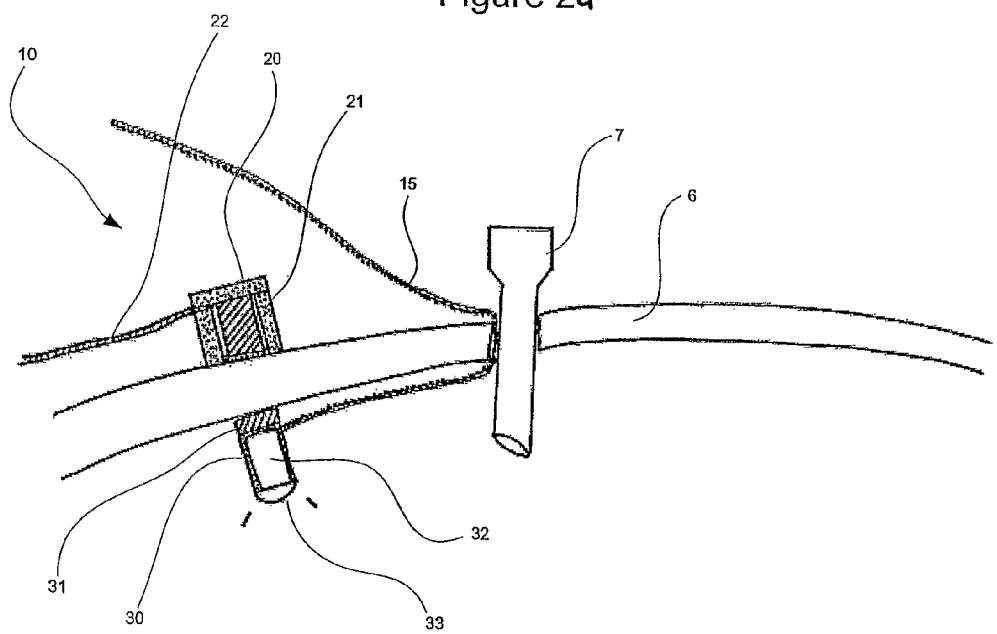
FIG. 2a is an exploded view of FIG. 1 typically with an open method of primary trocar introduction.
Figure 2B:
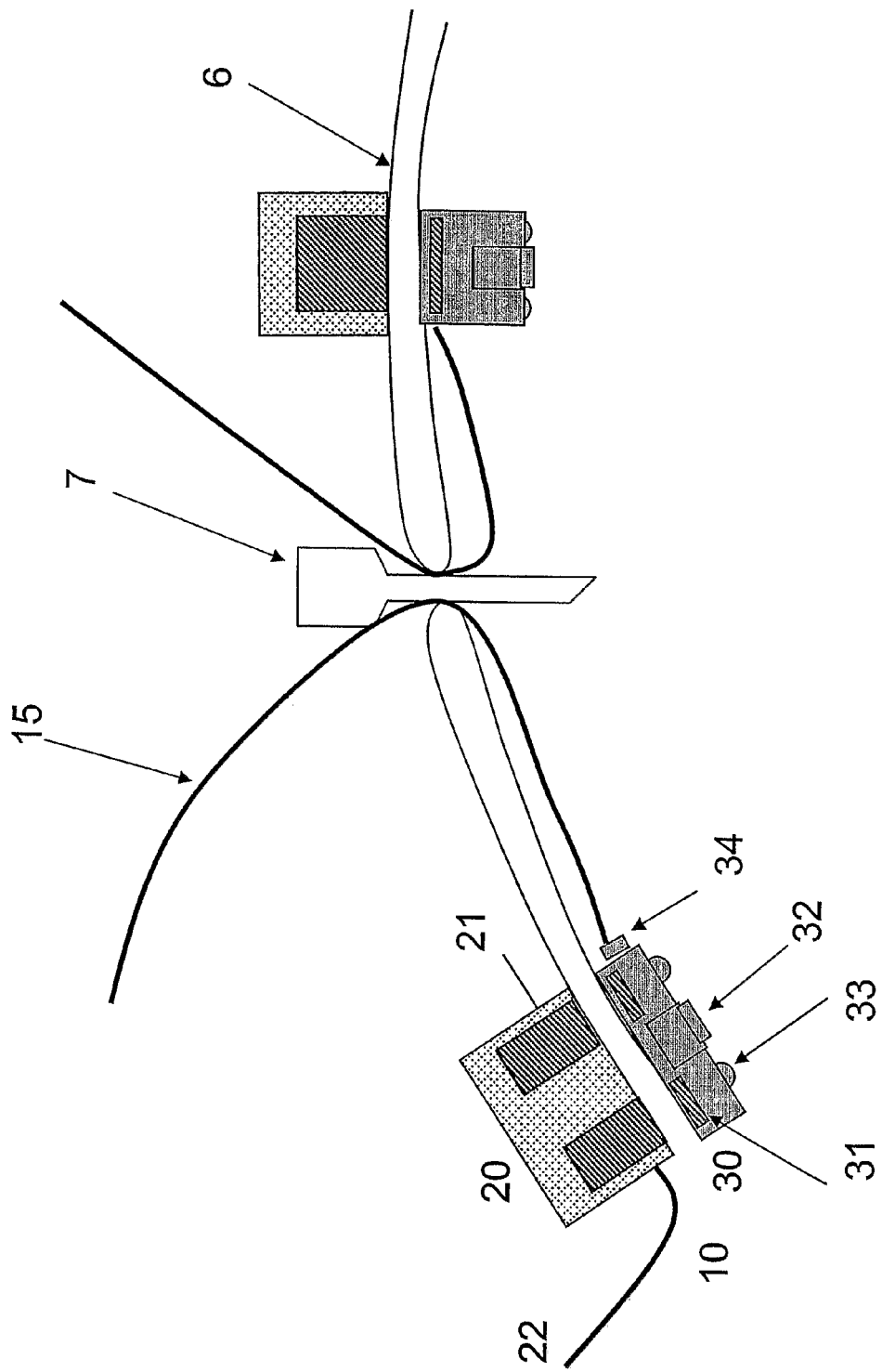
FIG. 2b is an exploded view of FIG. 1 typically with an open method of primary trocar introduction.

In the Hasson open method, the process is slightly different. No Veress needle is used. Carbon dioxide insulation comes after insertion of a blunt (not sharp) trocar/cannula combination. In this method, the second member 30 may be inserted into the abdominal cavity either before or after trocar/cannula placement. If the second member 30 is inserted before the trocar placement, the wire 15 may lie along side the trocar as shown in FIG. 2. Other, secondary access ports are then created, under direct vision using second member 30, and used for insertion of operating instruments, similar to the "blind" puncture described earlier. The handling device 50 may be used to engage the second member 30 using the secondary access ports. Referring to FIG. 2, it may be possible to have more than one device 10 used in a surgical operation. The design of a second device 10 may vary from the first device 10, for example, to take advantage of the default viewing angle.

If the first member 20 comprises an electromagnet 21, it is switched on once the second member 30 is within the body 5, and the second member 30 is magnetically engaged with the first member 20. Otherwise, if a permanent magnet 21 is used for the first member 20, the magnetic engagement is immediate once the first member 20 and the second member 30 are proximal to each other. Once magnetic engagement is established, the surgeon is able to control the movement and position of the second member 30 by moving the first member 20 across the body 5 of the patient.

If the second member 30 magnetically disengages from the first member 20, the surgeon may retrieve the second member 30 using the wire 15 as a guide. Alternatively, the abdominal cavity may be deflated to reduce the distance between the first and second members 20, 30. The first member 20 then engages the second member 30 again. Alternatively, the handling device 50 may be used to engage the second member 20 if complete visualization of the retrieval process is available. This may be provided by other second member 30 within the body 5 when more than one device 10 is used.

After the surgical procedure is completed, the surgeon removes the surgical instruments via the primary 7 and secondary cannulae. Next, the cannulae are removed from the access ports, and when the primary cannula 7 is removed from the first access port, the second member 30 may be removed from within the body 5. The surgeon moves the first member 20 towards the first access port until the second member 30 is reachable. Alternatively, if a flexible cable 15 is in use, the surgeon may simply pull the cable 15 to retrieve the second member 30 from within the body 5. Alternatively, the handling device 50 may be used to retrieve the second member 30 via the primary cannula 7. In this case, the second member 30 is removed from the body 5 before the primary cannula 7.

More than one device 10 may be used during a surgical procedure. Multiple devices 10 provide multiple views within the body. The multiple views are displayed at the same time on the display device 45. The display device is overlaid with a touch-sensitive screen that allows view selection by a surgical assistant by touching the display. The touch-sensitive screen is covered by a sterile plastic/transparent sheet. There is an intuitive means to correlate the camera view with the corresponding device 10 used during the surgery. This provides greater visual awareness to the surgeon to allow him or her to direct more attention on the surgical procedure thus possibly shortening the surgical time. A single handling device 50 may be used to deploy, re-position and retrieve more than one second member 30.

The first member 20 is held in place using a flexible mechanical arm 60, 62 and an attachment unit 63. The long stand 61 with base 64 and clamp 65 of the mechanical arm 60 are for attachment to the side of the patient bed. Multiple arms 60, 62 may be used for multiple first members. The flexible arm 60, 62 may be a robotic arm.

The second member 30 may also comprise of all LEDs 33 primarily to illuminate the body 5 within. Alternatively, the second member 30 may consist of a biopsy needle for tissue extraction or drug delivery. In this case, the handling device 50 and second member 30 may form a detachable surgical instrument.

Although it has been described that the first member 20 comprises the magnet 21, it is envisaged that the second member 30 may instead comprise a magnet 21 and the first member 20 comprise the magnetic material.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A device for laparoscopic or thoracoscope surgery, the device comprising: a first member to be moved across the body of a patient; and a second member to be placed within the body via a primary trocar using a handling device, the second member comprising an image capturing device to capture images from within the body and to transmit the captured images for display, the second member further comprising an attachment unit wherein the handling device manipulates the second member when the handling device is in releasable engagement with the attachment unit of the second member; wherein the second member is in magnetic engagement with the first member such that the movement of the second member within the body is in response to movement of the first member across the body, wherein the orientation of the second member is variable by changing the orientation of the first member, and wherein the orientation of the second member is variable using two magnets of different polarities for each of both first and second members.

2. The device according to claim 1, wherein the captured images are transmitted wirelessly to a display device.

3. The device according to claim 1, wherein power is supplied to the second member for the image capturing device by any one from the group consisting of: wirelessly from a power source, and a battery provided to the second member.

4. The device according to claim 1, wherein the second member is operatively connected to a display device and a power source via at least one flexible cable, and the cable provides convenient retrieval of the second member from within the body of the patient.

5. The device according to claim 1, wherein the first member comprises an electromagnet or permanent magnet, or a combination of an electromagnet and permanent magnet.

6. The device according to claim 5, wherein the strength of the magnetic force is varied to facilitate the movement of the second member.

7. The device according to claim 6, wherein the strength of the electromagnetic field is changed temporarily when movement of the first member is desired to enable the second member to move more freely.

8. The device according to claim 5, wherein if a permanent magnet is used, the distance between the magnets in the first and second members is varied to enable the second member to move more freely.

9. The device according to claim 1, wherein the image capturing device is a digital video camera.

10. The device according to claim 1, wherein the second member comprises a light emitting means to illuminate within the body.

11. The device according to claim 1, wherein the second member comprises an electromechanical probe to extract bodily tissue or to deliver drugs.

12. The device according to claim 11, wherein the electromechanical probe is a biopsy needle for tissue extraction.

13. The device according to claim 1, wherein a viewing angle of the image capturing device is adjustable by a first control provided on the first member.

14. The device according to claim 13, wherein the first control controls an actuator with ml embedded controller in the second member.

15. The device according to claim 1, wherein the orientation of the second member is varied by depressing the second member against the body to alter the viewing angle.

16. The device according to claim 1, further comprising a magnetic shield to limit undesirable magnetic interference to the image capturing device.

17. The device according to claim 1, wherein the device is fixed relative to the body using a flexible mechanical arm.

18. The device according to claim 17, wherein the mechanical arm is fastened to a side of the patient/surgical bed.

19. The device according to claim 1, further comprising a plurality of first and second members, wherein the plurality of second members are placed within the body via a primary trocar using a single handling device.

20. A device for laparoscopic or thoracoscope surgery, the device comprising: a first member to be moved across the body of a patient; and a second member to be placed within the body via a primary trocar using a handling device, the second member comprising an image capturing device to capture images from within the body and to transmit the captured images for display, the second member further comprising an attachment unit wherein the handling device manipulates the second member when the handling device is in releasable engagement with the attachment unit of the second member; wherein the second member is in magnetic engagement with the first member such that the movement of the second member within the body is in response to movement of the first member across the body, wherein image settings of the image capturing device is adjustable by a second control provided on the first member, the image settings being any from the group consisting of: zoom, focus, contrast, and brightness.

21. A device for laparoscopic or thoracoscope surgery, the device comprising: a first member to be moved across the body of a patient; and a second member to be placed within the body via a primary trocar using a handling device, the second member comprising an image capturing device to capture images from within the body and to transmit the captured images for display, the second member further comprising an attachment unit wherein the handling device manipulates the second member when the handling device is in releasable engagement with the attachment unit of the second member; wherein the second member is in magnetic engagement with the first member such that the movement of the second member within the body is in response to movement of the first member across the body, wherein the second member comprises a light emitting means to illuminate within the body, wherein the light intensity of the light emitting means is adjustable by a third control provided on the first member.

22. A system for laparoscopic or thoracoscope surgery, the system comprising: at least one device comprising: a first member to be moved across the body of a patient; and a second member to be placed within the body via a primary trocar using a handling device, the second member comprising an image capturing device to capture images from within the body and to transmit the captured images for display, the second member further comprising an attachment unit wherein the handling device manipulates the second member when the handling device is in releaseable engagement with the attachment unit of the second member the second member further comprising an assembly for operative attachment to a handling device; wherein the second member is in magnetic engagement with the first member such that movement of the second member within the body is in response to movement of the first member, wherein the orientation of the second member is variable by changing the orientation of the first member, and wherein the orientation of the second member is variable using two magnets of different polarities for each of both first and second members.

23. The system according to claim 22, wherein the handling device is a rigid forceps or a customized device with a pair of pincers or tongs, for seizing and holding objects, or a modified rigid laparoscopic device with a camera located at a removed proximal end of the laparoscopic device.

24. The system according to claim 22, wherein the handling device comprises a mechanism for deploying, re-positioning and retrieving the second member into and from the body through an opening provided by a trocar.

25. The system according to claim 24, wherein the plurality of second members are placed within the body via a primary trocar using a single handling device.

26. A system, for laparoscopic or thoracoscope surgery, the system comprising: at least two devices, each device comprising: a first member to be moved across the body of a patient; and a second member to be placed within the body via a primary trocar using a handling device, the second member comprising an image capturing device to capture images from within the body and to transmit the captured images for display; the second member further comprising an attachment unit wherein the handling device manipulates the second member when the handling device is in releasable engagement with the attachment unit of the second member; the second member is in magnetic engagement with the first member such that the movement of the second member within the body is in response to movement of the first member across the body; wherein the at least two devices provide at least two different views within the body, wherein the orientation of the second member is variable by changing the orientation of the first member, and wherein the orientation of the second member is variable using two magnets of different polarities for each of both first and second members.

27. The system according to claim 26, wherein the at least two different views are displayed at the same time on a display device.

28. The system according to claim 26, wherein one of the at least two different views is selectable using a touch screen selection panel that has labeled the at least two different views on the touch screen.

* * * * *